US008312992B2

(12) United States Patent
Disch

(10) Patent No.: US 8,312,992 B2
(45) Date of Patent: Nov. 20, 2012

(54) CLIP HOLDER

(75) Inventor: Alexander Disch, Freiburg (DE)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 13/349,887

(22) Filed: Jan. 13, 2012

(65) Prior Publication Data

US 2012/0175481 A1    Jul. 12, 2012

Related U.S. Application Data

(63) Continuation of application No. PCT/EP2010/060589, filed on Jul. 21, 2010.

(30) Foreign Application Priority Data

Jul. 24, 2009 (DE) .................. 10 2009 035 756

(51) Int. Cl.
*A61B 17/122* (2006.01)

(52) U.S. Cl. ....................................... 206/339; 206/340

(58) Field of Classification Search .......... 206/338–347; 606/157, 143, 158, 75, 142, 219; 248/316.4, 248/316.7, 687, 561, 74.2
See application file for complete search history.

(56) References Cited

U.S. PATENT DOCUMENTS

| | | | | |
|---|---|---|---|---|
| 3,363,628 | A | * | 1/1968 | Wood .............................. 606/158 |
| 4,146,130 | A | * | 3/1979 | Samuels et al. ................ 206/340 |
| 4,212,390 | A | | 7/1980 | Raczkowski et al. |
| 4,361,229 | A | | 11/1982 | Mericle |
| 4,696,396 | A | | 9/1987 | Samuels |
| 4,936,447 | A | | 6/1990 | Peiffer |
| 4,961,499 | A | | 10/1990 | Kulp |
| 4,972,949 | A | | 11/1990 | Peiffer |
| 5,201,416 | A | | 4/1993 | Taylor |
| 5,441,509 | A | | 8/1995 | Vidal et al. |
| 5,908,430 | A | | 6/1999 | Appleby |
| 6,158,583 | A | | 12/2000 | Forster |
| 6,273,253 | B1 | | 8/2001 | Forster et al. |
| 6,460,700 | B2 | | 10/2002 | Weisshaupt |
| 2002/0017472 | A1 | | 2/2002 | Weisshaupt |
| 2002/0046961 | A1 | | 4/2002 | Levinson et al. |
| 2006/0124485 | A1 | | 6/2006 | Kennedy |
| 2008/0312670 | A1 | | 12/2008 | Lutze et al. |
| 2011/0087244 | A1 | | 4/2011 | Weisshaupt et al. |

FOREIGN PATENT DOCUMENTS

| | | |
|---|---|---|
| DE | 0 494 243 | 12/1996 |
| DE | 690 29 474 | 7/1997 |
| DE | 199 03 752 | 3/2000 |

(Continued)

*Primary Examiner* — Terrell McKinnon
*Assistant Examiner* — Ingrid M Weinhold
(74) *Attorney, Agent, or Firm* — Lipsitz & McAllister, LLC

(57) ABSTRACT

The invention relates to a medical or surgical clip holder, comprising at least one holding device for holding at least one medical or surgical clip, the at least one holding device comprising at least two holding surface areas movable relative to each other for holding the at least one clip with force locking and/or positive locking, wherein the at least one holding device comprises at least one restoring device for moving the at least two holding surface areas relative to each other into a force-neutral position in which the at least one restoring device holds the at least two holding surface areas in a predefined position relative to each other following deflection of the at least two holding surface areas relative to each other from an initial position into a deflected position.

22 Claims, 6 Drawing Sheets

FOREIGN PATENT DOCUMENTS

| | | |
|---|---|---|
| DE | 101 05 235 | 8/2002 |
| DE | 697 13 608 | 2/2003 |
| DE | 20 2006 011 054 | 10/2006 |
| DE | 10 2006 001 344 | 7/2007 |
| DE | 20 2007 007 097 | 8/2007 |
| DE | 20 2008 004 929 | 7/2008 |
| DE | 10 2008 018 158 | 10/2009 |

* cited by examiner

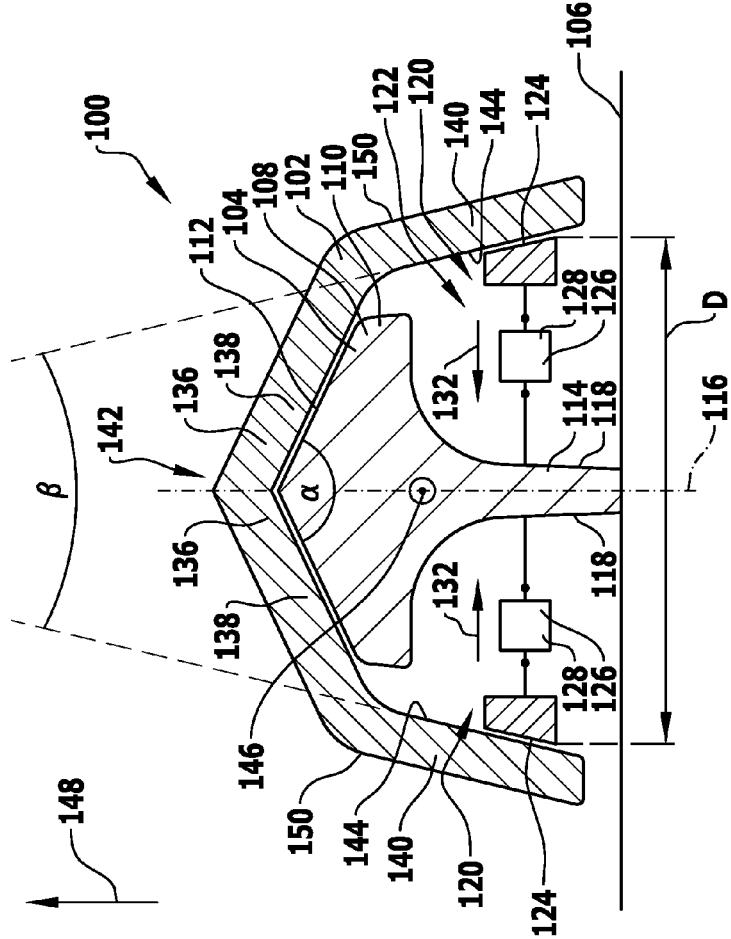
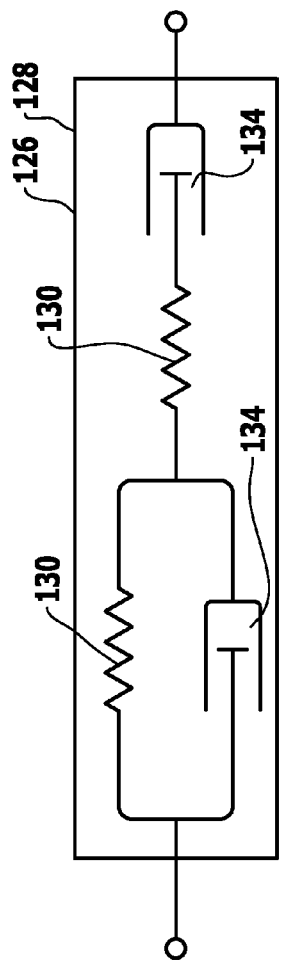
FIG.1
FIG.2

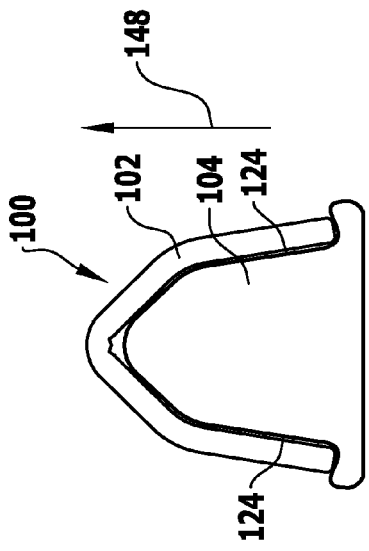
FIG.5a
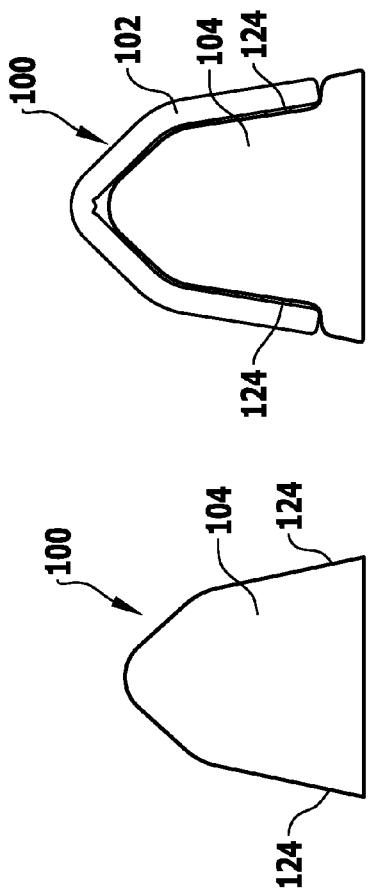
FIG.5b
FIG.5c
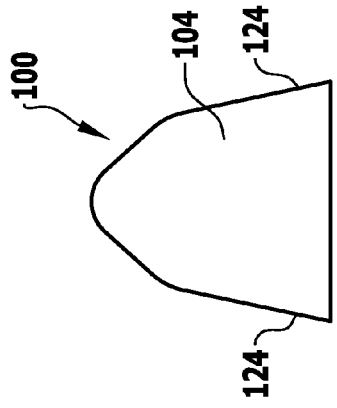
FIG.5d
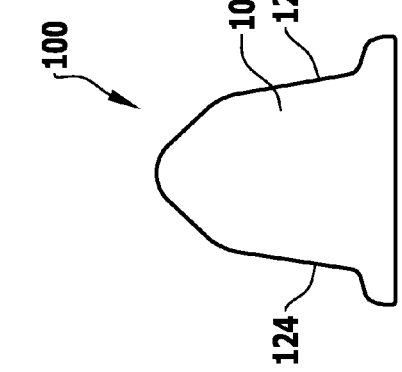
FIG.5e
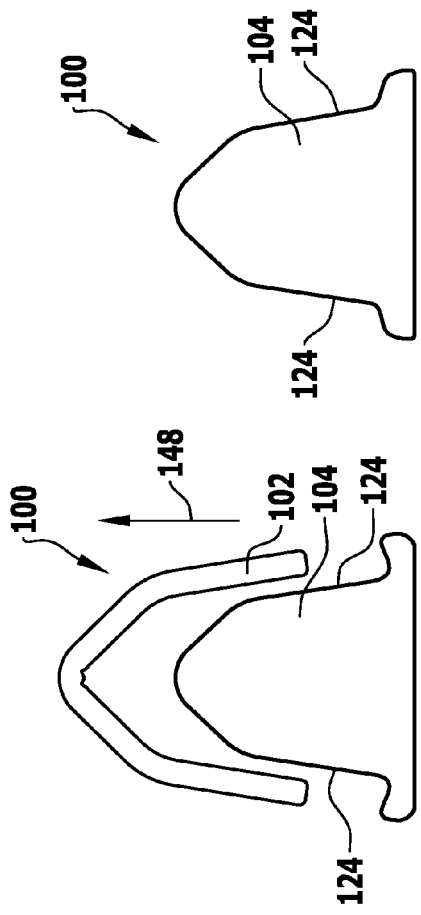
FIG.5f

CLIP HOLDER

CROSS-REFERENCE TO RELATED APPLICATIONS

This application is a continuation of international application number PCT/EP2010/060589 filed on Jul. 21, 2010 and claims the benefit of German application number 10 2009 035 756.4 filed on Jul. 24, 2009.

The present disclosure relates to the subject matter disclosed in international application number PCT/EP2010/060589 of Jul. 21, 2010 and German application number 10 2009 035 756.4 of Jul. 24, 2009, which are incorporated herein by reference in their entirety and for all purposes.

BACKGROUND OF THE INVENTION

The present invention relates to a medical or surgical clip holder comprising at least one holding device for holding at least one medical or surgical clip generally, and more specifically to a surgical clip holder with at least one holding device which comprises at least two holding surface areas movable relative to each other for holding the at least one clip with force locking and/or positive locking and at least one restoring device for moving the at least two holding surface areas relative to each other.

BACKGROUND OF THE INVENTION

Such clip holders serve, in particular, to store a supply of medical or surgical clips (also called "ligature clips", "ligating clips", "(hemostatic) clips" or "clips") and are known from the prior art.

In the clip holders known from the prior art, the clips are held, for example, by a frictional connection on elastic clamping devices of the clip holder, so that when a clip is removed from the clip holder, the frictional effect of the respective clamping device causes material abrasion from the clamping device and therefore contamination of the clip and/or damage to the clip. In particular, with the clip holders known from the prior art, when the elastic clamping devices engage outer sides of the clips, it may, furthermore, be necessary during the entire process of removing a clip, for the elastic clamping devices to be held away by an applicator receiving the clip. Simple and safe clip removal is therefore impeded by the elastic clamping devices.

SUMMARY OF THE INVENTION

In a first aspect of the invention, a medical or surgical clip holder comprises at least one holding device for holding at least one medical or surgical clip. Said at least one holding device comprises at least two holding surface areas movable relative to each other for holding the at least one clip with at least one of force locking and positive locking. Said at least one holding device comprises at least one restoring device for moving the at least two holding surface areas relative to each other into a force-neutral position in which the at least one restoring device holds the at least two holding surface areas in a predefined position relative to each other following deflection of the at least two holding surface areas relative to each other from an initial position into a deflected position. Said at least one holding device comprises at least one damping device counteracting said at least one restoring device for damping a movement of the at least two holding surface areas relative to each other from the deflected position back in the direction of the initial position.

In a second aspect of the invention, a method of removing a medical or surgical clip from a holding device of a medical or surgical clip holder for at least one medical or surgical clip is provided. According to said method at least two holding surface areas of the holding device are deflected relative to each other to release a connection with at least one of force locking and positive locking between the clip and the holding device. Moreover, the clip is removed from the holding device before the at least two holding surface areas return to an initial position existing before deflection.

BRIEF DESCRIPTION OF THE DRAWING FIGURES

The foregoing summary and the following description may be better understood in conjunction with the drawing figures, of which:

FIG. 1 shows a diagrammatic representation of a vertical section through a clip holder with a clip arranged on it;

FIG. 2 shows a diagrammatic representation of the Burger model to illustrate the viscoelasticity;

FIG. 5a shows a diagrammatic representation of a vertical section through the clip holder from FIG. 3 in an original state;

FIG. 5b shows a representation, corresponding to FIG. 5a, of the clip holder from FIG. 3 in a storage state in which a clip is held on the clip holder;

FIG. 5c shows a representation, corresponding to FIG. 5a, of the clip holder from FIG. 3, wherein the clip holder is additionally deformed before removal of the clip from the clip holder;

FIG. 5d shows a representation, corresponding to FIG. 5a, of the clip holder from FIG. 3, wherein the deformed clip holder in accordance with FIG. 5c does not immediately return to the original state after removal of the clip from the clip holder;

FIG. 5e shows a representation, corresponding to FIG. 5a, of the clip holder from FIG. 3, wherein the clip holder has partially returned to its original state after removal of the clip from the clip holder;

FIG. 5f shows a representation, corresponding to FIG. 5a, of the clip holder from FIG. 3, which after deformation due to arrangement and removal of a clip has returned to the original state again;

DETAILED DESCRIPTION OF THE INVENTION

Figure 3:
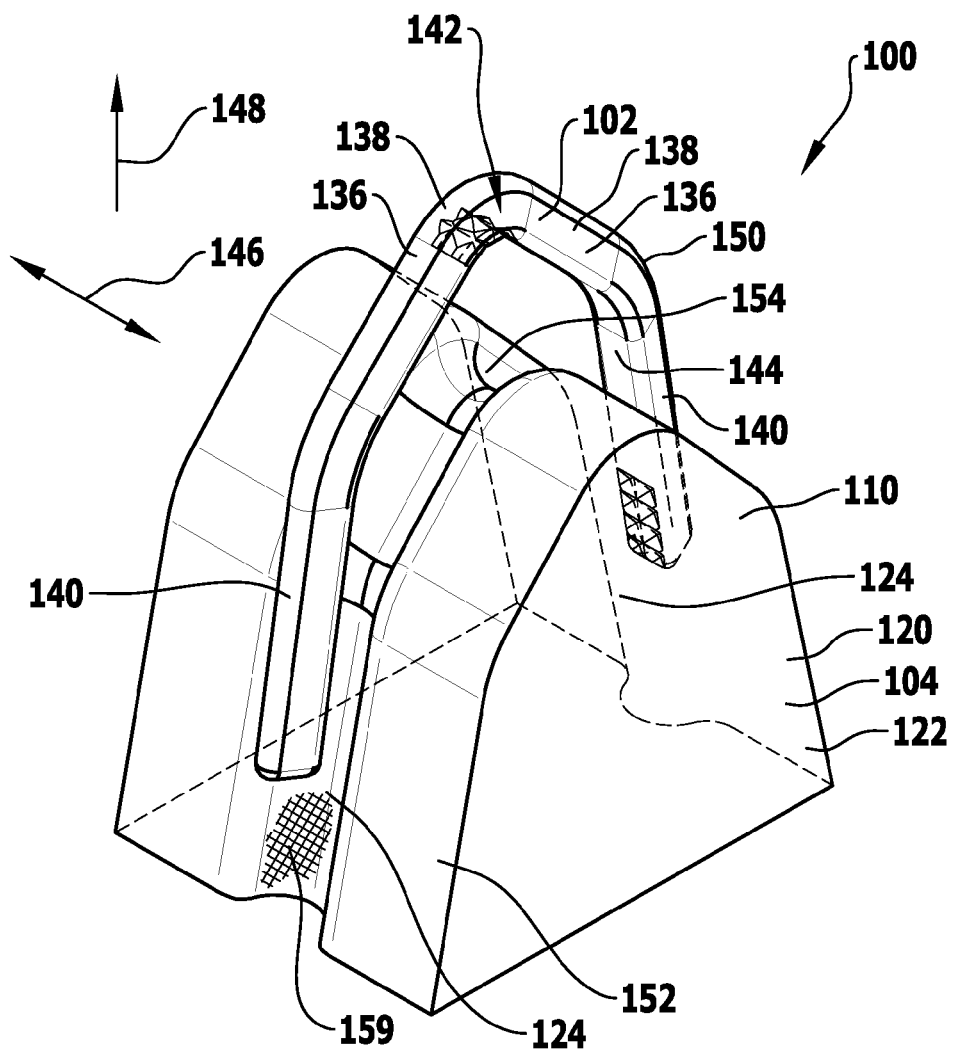
FIG. 3 shows a diagrammatic perspective representation of a clip holder with a ligature clip lifted off from it.

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a medical or surgical clip holder, comprising at least one holding device for holding at least one medical or surgical clip, said at least one holding device comprising at least two holding surface areas movable relative to each other for holding the at least one clip with at least one of force locking and positive locking, wherein said at least one holding device comprises at least one restoring device for moving the at least two holding surface areas relative to each other into a force-neutral position in which the at least one restoring device holds the at least two holding surface areas in a predefined position relative to each other following deflection of the at least two holding surface areas relative to each other from an initial position into a deflected position, and wherein said at least one holding device comprises at least one damping device counteracting said at least one restoring device for damping a movement of the at least two holding surface areas relative to each other from the deflected position back in the direction of the initial position.

Owing to the at least one holding device comprising at least one damping device, which counteracts action of the at least one restoring device, i.e., return movement of the at least two holding surface areas after deflection thereof, the movement of the at least two holding surface areas relative to each other after deflection back in the direction of the initial position is slowed down, so that a relaxation time which elapses after deflection of the at least two holding surface areas until the at least two holding surfaces areas have resumed a force-neutral position in which the at least one restoring device brings about no further movement of the at least two holding surface areas is increased. The at least one damping device is preferably so configured that the relaxation time of the at least two holding surface areas is greater, preferably considerably greater, for example, one order of magnitude greater, than a removal time required to remove at least one clip from the at least one clip holder.

Furthermore, owing to the at least one holding device comprising at least one damping device counteracting the at least one restoring device for damping a movement of the at least two holding surface areas relative to each other from the deflected position back in the direction of the initial position, in particular, also a reduction of the force acting by means of the at least one restoring device and the at least two holding surface areas on a clip held on the clip holder and, therefore, a reduction of the frictional effect holding the clip when the clip is being removed is ensured. This has the advantage that material abrasion from the clip holder is minimized when removing the at least one clip. Undesired contamination of the clip is therefore also reduced, in particular, completely avoided.

The initial position in which the at least two holding surface areas are arranged before they are deflected is preferably a force-neutral position in which a force applied by the at least one restoring device to the at least two holding surface areas is compensated by a force counteracting this force. In particular, it may be provided that this force counteracting the at least one restoring device is applied by a stop for the at least two holding surface areas and/or a clip arranged on the clip holder.

In a development of the invention, it is provided that the clip holder comprises a main body. At least one holding surface area is preferably configured so as to be movable relative to the main body. On the one hand, it may be provided that one of the at least two holding surface areas is firmly arranged on the main body, and the other one of the at least two holding surface areas is arranged so as to be movable on the main body. It is, however, preferable for the at least two holding surface areas to be configured so as to be movable relative to the main body. In this way, a clip arranged on the clip holder can be held in a particularly simple and flexible manner by the at least two holding surface areas.

A particularly simple arrangement of the at least one clip on the clip holder is, in particular, possible when the at least one holding device comprises a supporting surface for the at least one clip. In this way, in particular, a simple centering of the at least one clip on the at least one holding device of the clip holder is possible.

It is advantageous for at least one holding surface area of the at least one holding device to be part of the supporting surface for the at least one clip. In particular, when one of the at least two holding surface areas is firmly connected to the main body of the clip holder and only the other one of the at least two holding surface areas is configured so as to be movable relative to the main body, it can be provided that the holding surface area firmly arranged on the main body forms part of the supporting surface for the at least one clip.

It may be advantageous for at least one holding surface area to be oriented transversely to the support for the at least one clip, in particular, substantially perpendicularly to the supporting surface for the at least one clip. In this way, particularly easy positioning of the at least one clip for arrangement thereof on the clip holder is possible.

In an embodiment of the invention, it may be provided that at least one holding surface area is arranged opposite the supporting surface and, in particular, facing the supporting surface. In this way, the at least one clip to be arranged on the clip holder can be held particularly simply on the clip holder, for example, by the at least one clip being clamped between the supporting surface and the at least one holding surface area opposite the supporting surface.

It is advantageous for at least one holding surface area to be configured so as to be movable in the direction of the supporting surface. In this way, for example, a clip arranged at least partially between the at least one holding surface area and the supporting surface can be clamped particularly easily on the clip holder.

Alternatively or additionally, it may be provided that at least one holding surface area is configured so as to be movable away from the supporting surface. In particular, it may thus be provided that the at least one holding surface area is moved away from the supporting surface in order to clamp at least one clip between the at least one holding surface area and the supporting surface.

Furthermore, it may be provided that at least one holding surface area is configured so as to be movable parallel to the supporting surface. This is advantageous, in particular, when the function of the holding of the at least one clip with force locking and/or positive locking by the at least two holding surface areas movable relative to each other is to be implemented separately from the function of the supporting of the at least one clip on the at least one supporting surface.

The clip holder preferably comprises at least one supporting element, the surface of which forms at least part of the supporting surface for the at least one clip. The supporting element may, for example, be configured as part of the main body of the clip holder or be firmly or movably connected to the main body of the clip holder.

It is advantageous for the at least one supporting element to be made at least partially of an elastic material. In this way, in particular, deformation of the at least one supporting element when the at least one clip is being arranged on and/or removed from the clip holder is possible, so that manufacturing and/or handling inaccuracies can be compensated during both arrangement and removal.

It is advantageous for the at least one supporting element to comprise a top layer, the surface of which forms at least part of the supporting surface for the at least one clip. Use of a top layer for the at least one supporting element ensures that a base material of the at least one supporting element does not come into direct contact with the at least one clip to be arranged on the clip holder. Contamination of the at least one clip by the base material of the at least one supporting element is therefore effectively prevented by use of a top layer on the at least one supporting element.

The at least two holding surface areas of the at least one holding device are preferably arranged so as to face each other. In this way, in particular, a clip arranged between the at least two holding surface areas can be arranged particularly easily on the clip holder.

Alternatively, it may be provided that the at least two holding surface areas are arranged so as to face away from each other. In this way, in particular, a clip which engages around the at least two holding surface areas can be arranged on the clip holder. In this case, the at least two holding surface areas preferably engage opposite inner surfaces of the at least one clip arranged on the clip holder and hold the at least one clip, for example, by a connection with positive locking and/or force locking.

The at least two holding surface areas are preferably movable away from each other out of the initial position. In particular, when at least one clip is to be clamped between the at least two holding surface areas, the space required for arranging the at least one clip can be created by the at least two holding surface areas being movable away from each other out of the initial position. The at least two holding surface areas are then preferably moved towards each other by the at least one restoring device, so that the at least one clip arranged between the at least two holding surface areas is clamped between the at least two holding surface areas.

Alternatively or additionally, it may be provided that the at least two holding surface areas are movable towards each other out of the initial position. In particular, when the at least one clip engages around the at least two holding surface areas, so that in a storage state of the at least one clip, the at least two holding surface areas engage inner sides of the at least one clip, it may be provided that the at least two holding surface areas are movable towards each other in order to release a connection with positive locking and/or force locking between the at least two holding surface areas and the at least one clip. The at least two holding surface areas are then preferably moved towards each other by the at least one clip being deformed by an applicator such that the inner sides of the at least one clip which face each other and which the at least two holding surface areas engage are moved towards each other.

The at least one holding device preferably comprises at least one holding element, the surface of which forms at least part of at least one holding surface area. The at least one holding element is preferably arranged so as to be at least partly movable on the main body of the clip holder.

It is advantageous for the at least one holding element to be made at least partially of an elastic material. It may be provided that the elastic material forms at least part of the at least one restoring device of the at least one holding device.

It may be advantageous for the at least one holding element to comprise a top layer, the surface of which forms at least part of at least one holding surface area. In this way, any material can be selected as base material for the at least one holding element without taking into consideration the purity requirements for standard use of the medical or surgical clip, as the top layer prevents direct contact of the at least one clip arranged on the clip holder with the base material of the at least one holding element, so that the at least one clip arranged on the clip holder cannot be contaminated by the base material of the at least one holding element.

In an embodiment of the invention, it may be provided that the at least one restoring device and the at least one damping device are separate components of the at least one holding device.

Alternatively, it may be provided that the at least one restoring device is formed in one piece with the at least one damping device.

It is advantageous for the at least one restoring device and the at least one damping device to be made of the same material. In this way, the at least one restoring device and the at least one damping device and therefore the entire clip holder are particularly easy to manufacture.

The material of the at least one restoring device and/or of the at least one damping device is preferably a viscoelastic material. In this description and the appended claims, a viscoelastic material is to be understood as an elastic material which reassumes its initial shape only slowly following deformation.

In principle, all materials with a distinct viscoelastic behavior are usable.

In particular, it may be provided that the viscoelastic material comprises silicone, natural rubber, thermoplastic elastomers (TPE), polyethylene, polypropylene and/or polyurethane or is made of silicone, natural rubber, thermoplastic elastomers (TPE), polyethylene, polypropylene and/or polyurethane.

In an embodiment of the invention, it may be provided that the viscoelastic material is a foamed material. In particular, viscoelastic foams, also known as "slow recovery" foams, may be used. In this way, particularly simple manufacture of the clip holder is possible. In particular, it may be provided that the clip holder is produced in one piece from a foamable plastic material and is only partly foamed.

Alternatively or additionally, it may be provided that the viscoelastic material comprises a porous material.

In principle, it may be provided that for removal of a clip, the clip holder undergoes plastic deformation at least in sections, so that the clip holder does at least partially not return to an initial state.

It is advantageous for the viscoelastic material to be a material which returns substantially completely to an original state following deformation. The original state of the viscoelastic material is, in particular, that state of the viscoelastic material immediately after its manufacture. The viscoelastic material then preferably exhibits its maximum extent without the application of external force.

It is, furthermore, advantageous for the viscoelastic material to have a relaxation time of at least approximately 0.5 seconds following deformation of the viscoelastic material up until at least partial restoration of the original state. This ensures that the at least two holding surface areas, following deflection from an initial position to a deflected position, transfer sufficiently slowly to a force-neutral position, so that the at least one clip held on the clip holder can be removed from the clip holder following deflection of the at least two holding surface areas, before the at least two holding surface areas are placed by the at least one restoring device against the inner side of the clip again and produce an undesired frictional effect there.

The relaxation time may, in principle, be very long, so that the viscoelastic material undergoes at least approximately initial plastic deformation.

Alternatively, it may, however, also be advantageous for the viscoelastic material to have a relaxation time of at most approximately 2 seconds. In particular, for arranging at least one clip on the clip holder, it is thereby ensured that the at least two holding surface areas, following their deflection, are brought sufficiently quickly by the at least one restoring device into a force-neutral position, in particular, into the storage position in which the at least one clip is held by the at least two holding surface areas on the clip holder.

Particularly simple manufacture of the clip holder is possible, in particular, when the at least one holding device comprises a viscoelastic material or is made of a viscoelastic material.

The clip holder preferably comprises at least one clip or forms a set or a combination comprising at least one clip holder and at least one clip.

It is advantageous for the at least one clip to comprise two legs which include an original angle of less than 180° with each other. The original angle is that angle which is at least approximately included by the two legs of the at least one clip when the at least one clip is held on the clip holder. The original angle preferably corresponds at least approximately to that angle which the two legs of the at least one clip include when no force is acting on the clip.

In particular, when the at least one clip comprises two legs which include an original angle of less than 120° with each other, the at least one clip can be arranged particularly easily on the clip holder by the at least one clip engaging around the at least two holding surface areas. The at least two holding surface areas then preferably engage inner sides, which face each other, of the two legs of the at least one clip.

It is advantageous for the at least one clip to comprise a restoring device for restoring the original angle included by the two legs following deformation of the at least one clip.

In particular, it may be provided that a relaxation time of the at least one clip, which elapses following deformation of the at least one clip up until at least partial restoration of the original angle included by the two legs, is less than a relaxation time of the at least one holding device, which elapses following deflection of the at least two holding surface areas relative to each other up until at least partial return to the initial position. In this way, it is, in particular, ensured that the at least one clip can be lifted off from the clip holder before the at least two holding surface areas return to the initial state following their deflection, in particular, before the at least two holding surface areas, following their deflection and release of the connection between the at least one clip and the clip holder, engage the at least one clip again.

The at least one holding device preferably has a shape which is at least partially and at least approximately complementary to the shape of an inner side of the at least one clip. In this way, a particularly firm connection between the clip holder and the at least one clip and therefore a particularly secure hold of the at least one clip on the clip holder is possible when the at least one clip lies at least partially with its inner side against the at least one holding device.

At least one holding surface area preferably has a shape which is at least partially and at least approximately complementary to the shape of an inner side of the at least one clip. In particular, when the at least one holding surface area engages the inner side of the at least one clip to hold the at least one clip, a particularly secure force locking and/or positive locking can in this way be produced between the at least one clip and the clip holder.

Alternatively or additionally, it may be provided that at least one holding surface area has a shape which is at least partially and at least approximately complementary to an outer side of the at least one clip. In particular, when the at least one holding surface area engages the outer side of the at least one clip to hold the at least one clip, a particularly secure hold of the at least one clip on the clip holder is in this way possible by means of a force locking and/or positive locking.

In an embodiment of the invention, it may be provided that the clip holder comprises at least one coupling device for coupling the at least one clip to the at least one holding device. In particular, it may be provided that a positively locking connection can be produced between the at least one clip and the clip holder by means of the at least one coupling device.

The coupling device preferably comprises at least two coupling elements which can be brought into engagement with each other in a storage position of the at least one holding device in which the at least one clip is held on the at least one holding device. In this way, a particularly secure connection between the at least one clip and the clip holder is ensured, so that undesired lifting of the at least one clip off the clip holder is effectively prevented.

It is advantageous for at least one coupling element of the coupling device to be configured as a projection. In particular, when at least one coupling element of the coupling device is configured as a receptacle, particularly easy coupling of the at least one clip to the clip holder is possible.

At least one coupling element of the coupling device is preferably arranged on the at least one clip.

Alternatively or additionally, it may be provided that at least one coupling element of the coupling device is arranged on the at least one holding device.

In particular, it may be provided that the clip and/or the clip holder is/are provided with small shoulders and/or projections, so that a frictional connection and/or a positively locking connection is/are particularly easy to produce between the clip and the clip holder.

The present invention further relates to a method of removing a medical or surgical clip from a holding device of a medical or surgical clip holder for at least one medical or surgical clip, wherein at least two holding surface areas of the holding device are deflected relative to each other to release a connection with at least one of force locking and positive locking between the clip and the holding device, and wherein the clip is removed from the holding device before the at least two holding surface areas return to an initial position existing before deflection.

Undesired friction between the clip and the holding device and therefore undesired material abrasion and undesired contamination of the clip are avoided by the clip being removed from the holding device before the at least two holding surface areas return to an initial position existing before deflection.

The method in accordance with the invention preferably comprises the features and advantages described hereinabove in connection with the clip holder in accordance with the invention.

In particular, the method in accordance with the invention may have the advantage that an applicator with which the clip is removed from the clip holder need not be in contact with the at least two holding surface areas of the holding device throughout the entire duration of removal of the clip, in order to hold away the at least two holding surface areas, to release the connection with force locking and/or positive locking between the clip and the holding device. Harm to the applicator when removing the clip from the clip holder and, in particular, friction at the clip holder can thereby be avoided.

The time required for removal of a clip from the clip holder, in particular, the time between the applicator being introduced into the clip holder and the applicator completely leaving the clip holder with the clip, is preferably between approximately 0.5 seconds and approximately 2 seconds and depends, inter alia, on the size of the clip.

Owing to the deflection of the at least two holding surface areas by the applicator to remove the clip from the clip holder, an access area is preferably enlarged, so that it is easier for the applicator to engage the clip to be removed.

In the method in accordance with the invention, it may be provided that in order to release the connection with force locking and/or positive locking between the holding device and the clip, the clip is slidingly displaced relative to a main body of the clip holder in the direction opposite to a direction of removal. In particular, when the clip is at least approximately horseshoe-shaped, deflection of the at least two holding surface areas of the holding device and therefore release of the connection with force locking and/or positive locking between the clip and the holding device can be brought about by the sliding displacement of the clip relative to the main body of the clip holder in the direction opposite to the direction of removal.

Alternatively or additionally, it may be provided that in order to release the connection with force locking and/or positive locking between the holding device and the clip, the clip is tilted and/or rotated relative to a main body of the clip holder.

Furthermore, it may be provided that an original angle included by two legs of the clip is reduced in size in order to release the connection with force locking and/or positive locking between the holding device and the clip. An opening width of the clip is reduced in size, in particular, for a short time, so that the holding surface areas are deflected relative to each other.

It is particularly advantageous for a frictional effect between at least one holding surface area of the holding device and the clip, when removing the clip, to be reduced by at least approximately 50%, for example, by at least approximately 70%, in particular, by at least approximately 85%, preferably completely avoided, by the deflection of the at least two holding surface areas relative to each other to release the connection with force locking and/or positive locking between the holding device and the clip. In this way, material abrasion from the holding device and therefore contamination of the clip when removing the clip from the holding device are preferably completely avoidable.

The clip holder in accordance with the invention is suited, in particular, for performance of the method in accordance with the invention.

The clip holder in accordance with the invention is suited, in particular, for storing a supply of ligature clips, and both standard clips and double-web clips can preferably be arranged on a small common clip bench.

The clip holder in accordance with the invention is preferably cost-effective to manufacture and assemble. Furthermore, it is particularly easy to load the clip holder in accordance with the invention with at least one clip. The clip holder in accordance with the invention may, for example, be designed as a disposable part.

In particular, when the clip holder comprises a viscoelastic material which applies only a low holding force to the at least one clip, it may be provided that packaging, for example, a cover and/or a blister, is provided for safe storage of the at least one clip on the clip holder during transportation of the clip holder.

Release of the at least one clip from the clip holder as reaction to introduction of an applicator and engagement of the applicator on the at least one clip preferably takes place with a time dependence and just not only in direct interaction with the applicator.

The time dependence is achieved, in particular, by an inertly reacting viscoelastic material, and, in particular, the restoring of the holding surface areas which are arranged, for example, on contact elements, in order to secure the at least one clip on the clip holder, occurs with a time delay.

A positive locking between the at least one clip and the holding surface areas of the clip holder is preferably released at least for the duration of removal of the at least one clip from the clip holder.

The degree of frictional locking between the at least one clip to be held and the clip holder and/or the time dependence of the deformation of the clip holder, in particular, of the deflection of the at least one holding surface area and/or of the movement of the at least one supporting element of the clip holder, are preferably implemented by adapting the geometry of the clip holder to the at least one clip to be held, for example, by way of a defined frictional effect, which can bring about a delayed restoring, at a holding element deflected by the applicator.

In an embodiment of the invention it is provided that the clip holder is produced in one piece from a plastic material and that the inert behavior is implemented by an additionally attached viscoelastic body. The inert behavior of the holding surface areas is preferably achieved by a continuous viscoelastic body, for example, by an inserted foamed film.

In particular, when viscoelastic materials are used, it may be provided that the viscoelastic materials are not in direct surface contact with the clips but act via interposed, substantially non-viscoelastic elements. Here, in particular, a multi-layer structure of the clip holder is provided, with the individual layers differing in their material behavior, in particular, with respect to the viscoelasticity and/or the stiffness. In particular, it may be provided that a foamed material with an additional, non-foamed and yet deformable top layer is provided, and that only this top layer is in direct contact with the surface of the clip.

The clip holder in accordance with the invention is preferably of particularly simple construction and, in particular, does not comprise any movable, filigree retaining members.

In particular, when the clip holder is resiliently constructed and, in particular, does not comprise any rigid supporting surfaces for the at least one clip, the clip may, in particular, for removal from the clip holder, align itself to a slight extent with the applicator, so that improved transfer of the clip from the clip holder to the jaw parts of the applicator is possible.

Identical or functionally equivalent elements are denoted in all Figures by the same reference numerals.

FIG. 1 shows a medical or surgical clip holder 100 for at least one medical or surgical clip 102.

The clip holder 100 comprises a main body 104 which is arranged on a base plate 106.

The main body 104 comprises a supporting part 108 which forms a supporting element 110 for placement of at least one clip 102 on the clip holder 100.

An upper side of the supporting element 110 that faces away from the base plate 106 forms a supporting surface 112 of the clip holder 100 for placement of the clip 102 thereon.

The supporting part 108 of the main body 104 is arranged on the base plate 106 of the clip holder 100 by means of a web-shaped area 114 of the main body 104.

The clip holder 100 and, consequently, also the main body 104 are of at least approximately mirror-symmetrical configuration in relation to a longitudinal center plane 116 of the clip holder 100.

The longitudinal center plane 116 extends substantially perpendicularly to the base plate 106 of the clip holder 100.

At least one holding element 120 for holding the clip 102 is arranged at each of the opposite side faces 118 of the web-shaped area 114 of the main body 104.

The holding elements 120 together form a holding device 122 of the clip holder 100.

The surfaces of the holding elements 120 that face away from the web-shaped area 114 of the main body 104 of the clip holder 100 form holding surface areas 124 by means of which the holding elements 120 engage a clip 102 arranged on the clip holder 100.

The holding elements 120 each comprise a damping device 126 and a restoring device 128. The holding elements 120 are of deformable configuration, so that the holding surface areas 124 can be deflected from an initial position. The holding surface areas 124 can be returned to a predefined position by the restoring devices 128.

The damping devices 126 serve to damp the movement executed by the holding surface areas 124, after deflection from an initial position, as a result of the action of the restoring devices 128.

In the clip holder 100 shown in FIG. 1, it is, in particular, provided that the holding surface areas 124 are deflectable in the direction of the web-shaped area 114 of the main body 104 of the clip holder 100. After such deflection, the holding surface areas 124 are movable away from the web-shaped area 114 of the main body 104 of the clip holder 100 by the restoring devices 128. The force applied by the restoring devices 128 to the holding surface areas 124 to move these is dampable by the damping devices 126, so that the movement of the holding surface areas 124 from the deflected position to the initial position occurs at a slow speed.

The damping device 126 and the restoring device 128 of each holding element 120 are preferably formed in one piece from the same material, in particular, a viscoelastic material.

The Burger model shown in FIG. 2 as combination of the so-called Kelvin-Voigt model with the so-called Maxwell model may, for example, be used to describe the restoring properties and the damping properties of such a viscoelastic material.

In accordance with the Kelvin-Voigt model, a spring 130 is provided, which is arranged in a direction of load 132 parallel to a damper 134. This system in accordance with the Kelvin-Voigt model is connected in its entirety in series in the direction of load 132 to a further spring 130 and to a damper 134 in accordance with the Maxwell model which is connected in series in the direction of load.

The material which the holding elements 120 comprise or from which the holding elements 120 are at least partially formed can be described particularly simply by means of this system of springs 130 and dampers 134 in accordance with the Burger model. Following deformation of the viscoelastic material, the springs 130 cause the return to the initial state known from elastic materials. The dampers 134 serve to slow down the return movement, so that the material is not elastic, but viscoelastic.

As shown in FIG. 1, a clip 102 can be arranged on the clip holder 100 described above.

The clip 102 is preferably at least approximately horseshoe-shaped and in a storage state on the clip holder 100 is at least approximately mirror-symmetrical in relation to the longitudinal center plane 116 of the clip holder 100.

The clip 102 comprises two legs 136 which each have a middle section 138 and an end section 140.

In the storage state of the clip 102 on the clip holder 100, the middle sections 138 of the legs 136 of the clip 102 are connected to each other in the area of the vertical longitudinal center plane 116 and include an angle α of, for example, 120° with each other.

The end sections 140 of the legs 136 of the clip 102 are arranged at ends of the middle sections 138 of the legs 136 that are remote from each other and include an angle β of, for example, approximately 30° with each other.

The clip 102 is preferably made of a metallic material, so that the clip 102 comprises a restoring device 142 which returns the clip 102 after deformation at least approximately to the initial state. In particular, it is provided that following deformation of the clip 102, by which the angle α, included by the middle sections 138 of the legs 136 of the clip 102, is reduced in size, the restoring device 142 returns the clip 102 to the initial position in which the angle α has the predefined value of the initial position.

In the storage state of the clip 102 on the clip holder 100, shown in FIG. 1, the clip 102 rests with an inner side 144 in the area of the middle sections 138 of the legs 136 of the clip 102 on the supporting surface 112 of the supporting element 110, i.e., on the upper side of the supporting part 108 of the main body 104 that faces away from the base plate 106.

To this end, the supporting element 110 is preferably so configured that the supporting surface 112 of the supporting element 110 has at least approximately a shape which is at least approximately complementary to a shape of the inner side 144 of the clip 102 in the area of the middle sections 138 of the legs 136 of the clip 102.

The supporting element 110 is, for example, made of an elastic material, so that, in particular, when arranging the clip 102 on the clip holder 100, it is possible to compensate particularly easily for inaccuracies of handling.

In the state of the clip 102 on the clip holder 100, shown in FIG. 1, the holding elements 120 lie with the holding surface areas 124 against the inner sides 144 of the clip 102 in the area of the end sections 140 of the legs 136 of the clip 102.

Since the holding surface areas 124 in the storage state of the clip 102 on the clip holder 100 shown in FIG. 1 are not arranged in their original position in which they are at a maximum distance from the longitudinal center plane 116, but instead are deflected in the direction of the longitudinal center plane 116 by the end sections 140 of the legs 136 of the clip 102, the restoring device 128 generates a force directed away from the longitudinal center plane 116, which presses the holding surface areas 124 against the inner side 144 of the clip 102 in the area of the end sections 140 of the legs 136 of the clip 102. In this way, a frictional effect is created, which holds the clip 102 on the clip holder 100 by means of at least a frictional connection, preferably, in particular, by means of a positively locking connection.

The clip holder 100 extends along a longitudinal axis 146 running in the longitudinal center plane 116 and parallel to the base plate 106 over a length of, for example, 2 to 5 cm, so that a plurality of clips 102, for example, 8 or 10 clips 102, can be arranged next to one another in a row on the clip holder 100.

The clip holder 100 shown in FIG. 1 is used as follows:

After manufacture of the clip holder 100 and before arrangement of clips 102 on the clip holder 100, the holding surface areas 124 of the holding elements 102 of the clip holder 100 are arranged in an original position in which a distance D of the holding surface areas 124 from each other is at a maximum.

In particular, the distance D of the holding surface areas 124 from each other in the original position is greater than the distance between the end sections 140 of the legs 136 of the clip 102, which the holding surface areas 124 engage in the storage state of the clip 102 on the clip holder 100.

To load the clip holder 100 with a clip 102, the clip 102 is placed in the direction opposite to a direction of removal 148 extending perpendicularly to the base plate 106 with its inner side 144 on the clip holder 100.

The clip 102 comes to rest with the inner side 144 in the area of the middle sections 138 of the legs 136 of the clip 102 on the supporting surface 112 of the supporting element 110 of the clip holder 100.

Owing to the comparatively short distance between the end sections 140 of the legs 136 of the clip 102 in the areas in which the holding surface areas 124 engage the inner side 144 of the clip 102, the holding elements 120 undergo deformation when the clip 102 is placed on the clip holder 100.

The holding surface areas 124 are thereby deflected in the direction of the longitudinal center plane 116, so that the distance D of the holding surface areas 124 from each other is reduced in size.

The restoring devices 128 of the holding elements 120 subsequently generate a force which moves the holding surface areas 124 away from the longitudinal center plane 116 and presses them against the inner side 144 of the clip 102 in the area of the end sections 140 of the legs 136 of the clip 102.

The force transferred to the clip 102 by the restoring device 128 brings about a frictional connection of the clip 102 to the clip holder 100.

The damping device 126 slows down the restoring of the holding surface areas 124 by the restoring devices 128, so that when the clip 102 is placed on the clip holder 100, a frictional effect between the holding surface areas 124 and the inner side 144 of the clip 102 and, consequently, also a material abrasion from the holding surface areas 124 caused by the clip 102 can be minimized by an additional deflection of the holding surface areas 124.

The clip 102 is removed from the clip holder 100 as follows:

With an applicator (not shown in FIG. 1) a doctor wishing to remove the clip 102 from the clip holder 100 engages an outer side 150 of the clip 102 that faces away from the inner side 144 of the clip 102.

In doing so, he preferably deforms the clip 102 such that the angle α, included by the middle sections 138 of the clip 102, is reduced in size, and the end sections 140 of the legs 136 of the clip 102 thus move towards each other.

The holding surface areas 124 are thereby moved towards each other, i.e., the distance D between the holding surface areas 124 is reduced in size.

Once the doctor stops applying the force causing the deformation of the clip 102, the restoring device 142 of the clip 102 causes the middle sections 138 of the legs 136 of the clip 102 to include the predefined angle α included in the initial position and the end sections 140 of the legs 136 of the clip 102 to move apart again.

The restoring device 142 of the clip 102 does not interact with a damping device, so that the restoring of the clip 102 after release of the force causing the deformation occurs substantially instantaneously.

However, since the holding elements 120 have a damping device 126, which counteracts the action of the restoring device 128 of the holding elements 120, the restoring of the holding surface areas 124 does not occur instantaneously but with time delay.

The different restoring of the clip 102 and the holding elements 120 to the position existing before the deflection causes the holding surface areas 124 to be released from the inner side 144 of the clip 102.

Consequently, the frictional connection between the clip 102 and the clip holder 100 is released.

The clip 102 is, therefore, particularly easy to remove from the clip holder 100 at least until the restoring device 128 has slowly returned the holding surface areas 124 to the initial position.

In a corresponding geometrical configuration (not shown in FIG. 1) of the clip 102 and/or the holding elements 120, it is also conceivable for the holding elements 120 to hold the clip 102 by means of a positively locking connection on the clip holder 100.

In particular, when the clip 102 is merely held by means of a frictional connection on the clip holder 100, a packaging (not shown), for example, a blister may be provided, which additionally secures the clip 102 for transportation of the clip holder 100 with the clip 102.

Such a packaging is then removed before the clip holder 100 is used and the clip 102 is removed from the clip holder 100.

A clip holder 100 shown in FIG. 3 differs from the clip holder 100 shown in FIG. 1 in that the supporting element 110 and the holding elements 120 are constructed in one piece.

The main body 104 which, consequently, comprises the holding elements 120 and the supporting element 110 is preferably made entirely of a viscoelastic material.

A surface 152 of the main body 104 preferably has an at least approximately horseshoe-shaped cross section taken in a plane perpendicular to the longitudinal axis 146, so that the surface 152 of the main body 104 has at least approximately a shape which corresponds at least approximately to a shape of the inner side 144 of the clip 102.

When the clip holder 100 shown in FIG. 3 is loaded with the clip 102, i.e., the clip 102 is placed on the clip holder 100 in the direction opposite to the direction of removal 148, the main body 104 of the clip holder 100 is deformed in such a way that a depression 154 forms in the surface 152 of the main body 104, the shape of which is at least approximately complementary to the inner side 144 of the clip 102.

The surface 152 of the main body 104 then forms in the area of the depression 154, on the one hand, the holding surface areas 124 of the holding elements 120 of the clip holder 100 and, on the other hand, also the supporting surface 112 of the supporting element 110 of the clip holder 100.

Owing to the viscoelastic properties of the material of the main body 104, after the deformation due to placement of the clip 102, the main body 104 spreads out until the surface 152 nestles against the inner side 144 of the clip 102 in the area of the depression 154.

Owing to the restoring devices 128 of the holding elements 120, which, in the clip holder 100 shown in FIG. 3, are implemented by the viscoelastic material of the main body 104, the surface 152 is pressed in the area of the depression 154 against the inner side 144 of the clip 102 so that the clip 102 is held by a frictional connection on the clip holder 100.

The clip 102 can be removed from the clip holder 100 using an applicator 156 (shown in FIG. 4) for use by a doctor during an operation.

To do so, the doctor grips the outer sides 150 of the clip 102 with jaw parts 158 of the applicator 156 and in doing so deforms the clip in such a way that the angle α included by the middle sections 138 of the legs 136 of the clip 102 is reduced in size and the end sections 140 of the legs 136 of the clip 102 approach each other.

In particular, when the clip 102, as shown in FIG. 3, has an open V-shape in the direction opposite to the direction of removal 148 in the storage state of the clip 102 on the clip holder 100, for removal from the clip holder 100, the clip can also be pressed onto the main body 104 in the direction opposite to the direction of removal 148.

In both cases, i.e., either by deformation of the clip 102 or by displacement of the clip 102 in the direction opposite to the direction of removal 148 onto the main body 104 of the clip holder 100, a deflection of the holding surface areas 124 of the holding elements 120 of the clip holder 100 towards each other is brought about.

Since both the return of the angle α to the initial position by means of the restoring device 142 and a lifting of the clip 102 in the direction of removal 148 off the clip holder 100 occur substantially instantaneously, and, after the deflection brought about by the deformation of the clip 102, the holding surface areas 124 return to the initial position with a time delay owing to the action of the damping devices 126 of the holding elements 120, the deformation of the clip or the movement of the clip 102 in the direction opposite to the direction of removal 148 causes the frictional connection of the clip 102 to the clip holder 100 to be released, so that the clip 102 can be removed particularly easily from the clip holder 100, and, in particular, no abrasion whatsoever from the holding surface areas 124 of the clip holder 100 occurs and, consequently, no contamination of the clip 102.

Figure 4:
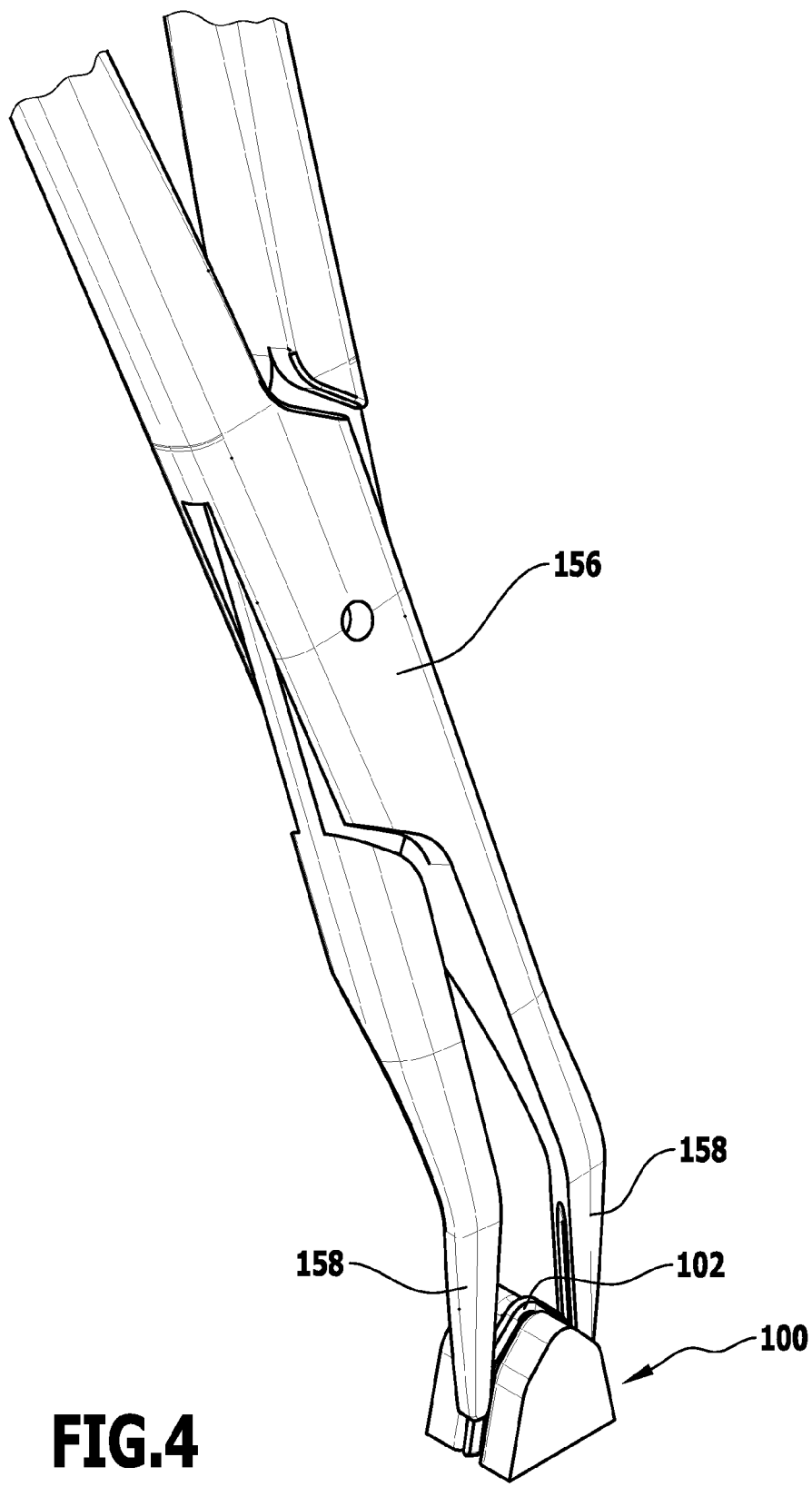
FIG. 4 shows a diagrammatic perspective representation of the clip holder from FIG. 3, with an applicator engaging the clip to remove it from the clip holder.

The different stages of use of the clip holder 100 in accordance with the embodiment shown in FIGS. 3 and 4 are represented in FIGS. 5a to 5f.

FIG. 5a shows an original position of the main body 104 of the clip holder 100, in which the main body 104 has no deformations whatsoever. In this original position, the holding surface areas 124 are at a maximum distance D from each other.

FIG. 5b shows a storage position of the clip holder 100, in which the main body 104 of the clip holder 100 is so deformed by the loading of the clip holder 100 with a clip 102 that the clip 102 is held by a frictional connection on the main body 104 of the clip holder 100. The surface 152 of the main body 104 lies directly against the inner side 144 of the clip 102 in the area of the depression 154 and thus produces a frictional connection between the clip 102 and the clip holder 100.

FIG. 5c shows an additional deformation of the main body 104 of the clip holder 100 as a result of the clip 102 being moved in the direction opposite to the direction of removal 148 before removal. The main body 104 of the clip holder 100 is thereby compressed in the direction opposite to the direction of removal 148. As a result, the holding surface areas 124 of the holding elements 120 of the clip holder 100 are deflected towards each other, so that the frictional connection between the clip 102 and the clip holder 100 is released and the clip 102 can be removed particularly easily and without any material abrasion from the main body 104 of the clip holder 100.

FIG. 5d shows the clip holder 100 with the clip 102 after removal of the clip 102 from the clip holder 100 in order to illustrate that after removal of the clip 102 from the clip holder 100 the main body 104 does not return immediately to the original state, which would make simple lifting of the clip 102 off the main body 104 of the clip holder 100 difficult. Instead, owing to the viscoelastic properties of the main body 104, the main body 104 of the clip holder 100 initially remains briefly in the deformed position and owing to the action of the damping devices 126 implemented by the viscoelastic material of the main body 104 returns very slowly, after assuming a transitional state (shown in FIG. 5e), to the original position (shown in FIG. 5f).

In particular, when the main body 104 of the clip holder 100 is made at least almost entirely of a viscoelastic material, it may be provided that the main body 104 is provided with a top layer 159 (indicated in FIG. 3), in order to avoid direct contact between the viscoelastic material of the main body 104 of the clip holder 100 and the clip 102. In this way, a particularly advantageous viscoelastic material can be selected without having to take into account the particular cleanliness that is required for later use of the clip 102.

Aside from that, the clip holder 100 shown in FIGS. 3, 4, 5a to 5f corresponds with respect to construction and function to the clip holder 100 shown in FIG. 1, to the above description of which reference is made in this connection.

Figure 6:
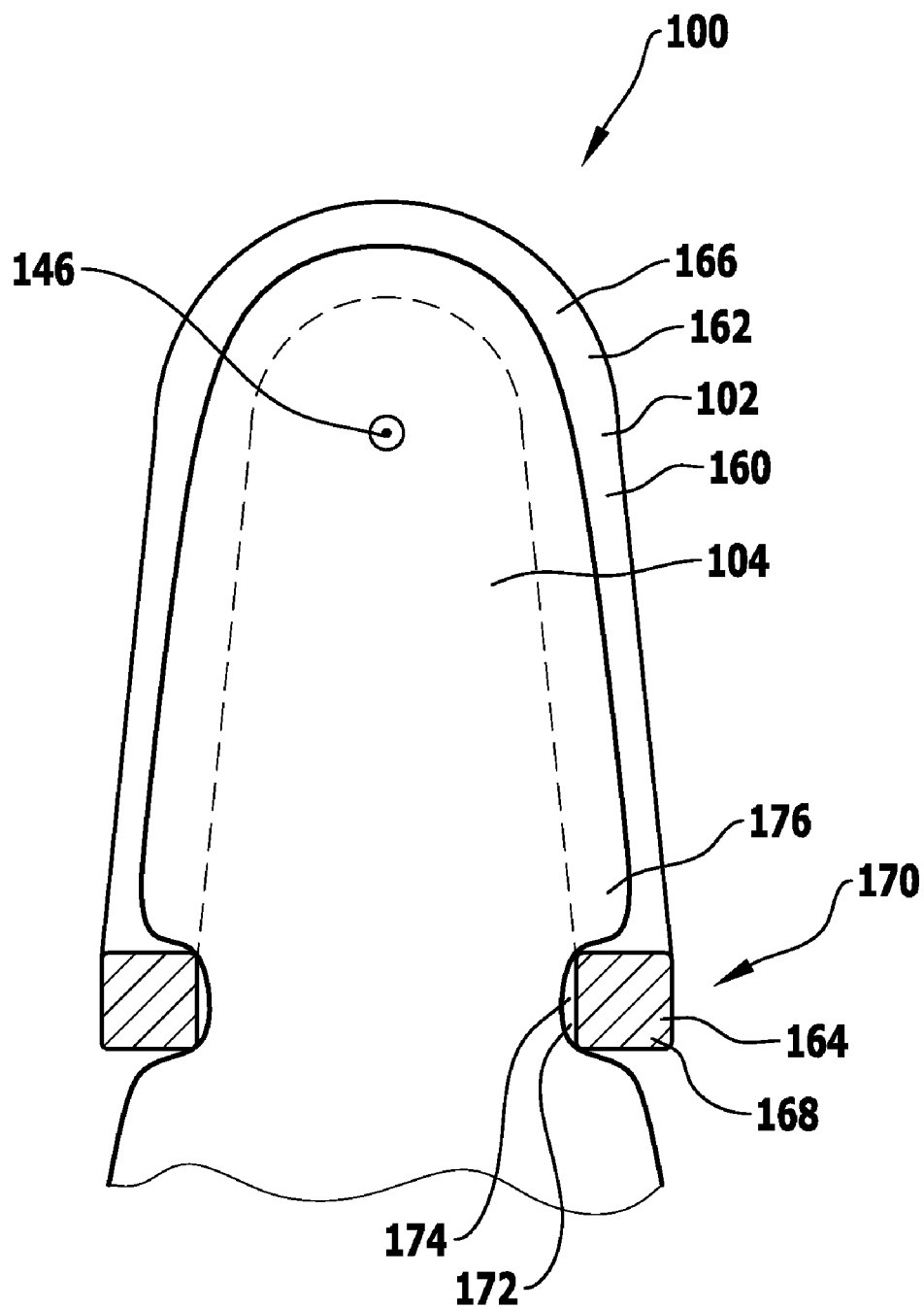
FIG. 6 shows a representation, corresponding to FIG. 5b, of a clip holder with a clip of double-web configuration arranged on the clip holder.

A clip holder 100 shown in FIG. 6 differs from the clip holder 100 shown in FIGS. 3, 4, 5a to 5f in that the main body 104 of the clip holder 100 has a substantially parabolic cross section taken in a plane oriented perpendicularly to the longitudinal axis 146. The clip holder 100 shown in FIG. 6 is particularly well suited for arrangement of clips 102 configured as double-web clips 160.

Such double-web clips 160, known, for example, from DE 10 2006 001 344 A1, are formed substantially by two horseshoe-shaped clips 102, as described above, each of which forms a web 162 of the double-web clip 160. The webs 162 are connected to each other in connection areas 164 at their ends, facing away from the middle sections 138, of the end sections 140 of the legs 136.

Formed between the horseshoe-shaped webs 162 of the double-web clip 160 extending parallel to each other is a gap 166 into which the main body 104 of the clip holder 100 can spread out when the double-web clip 160 is placed on the main body 104 of the clip holder 100. The representation in FIG. 6 shows a diagrammatic vertical section perpendicular to the longitudinal axis 146 through the clip holder 100 with the double-web clip 160 in the area of the gap 166 between the webs 162.

As shown in FIG. 6, a positively locking connection is enabled between the double-web clip 160 and the main body 104 of the clip holder 100 by the main body 104 of the clip holder 100 spreading out into the gap 166 of the double-web clip 160.

The connection area 164 of the double-web clip 160 forms a first coupling element 168 of a coupling device 170. The first coupling element 168 is arranged in a receptacle 174 of the main body 104, which is configured as a recess and forms a second coupling element 172.

In the coupling device 170 shown in FIG. 6, the positively locking connection of the clip 102 to the clip holder 100 is produced by a projection 176 arranged in the direction of removal 148 before the receptacle 174 and extending into the gap 166 of the double-web clip 160.

In particular, when the geometrical shape of the clip 102 and/or the geometrical shape of the holding elements 120 enable a positively locking connection of the clip 102 to the clip holder 100, a force acting on the clip 102, in the storage state of the clip 102 on the clip holder 100, which produces a frictional connection between the clip 102 and the clip holder 100, may be dispensed with.

In particular, it can thus be provided in the clip holder 100 shown in FIG. 6 that the main body 104 is only made of a viscoelastic material in the area of the projection 176 because a firm hold of the clip 102 on the clip holder 100 is already ensured by the main body 104 spreading out in the area of the projection 176.

Aside from that, the clip holder 100 shown in FIG. 6 corresponds with respect to construction and function to the clip holder 100 shown in FIGS. 3, 4, 5a to 5f, to the above description of which reference is made in this connection.

Figure 7:
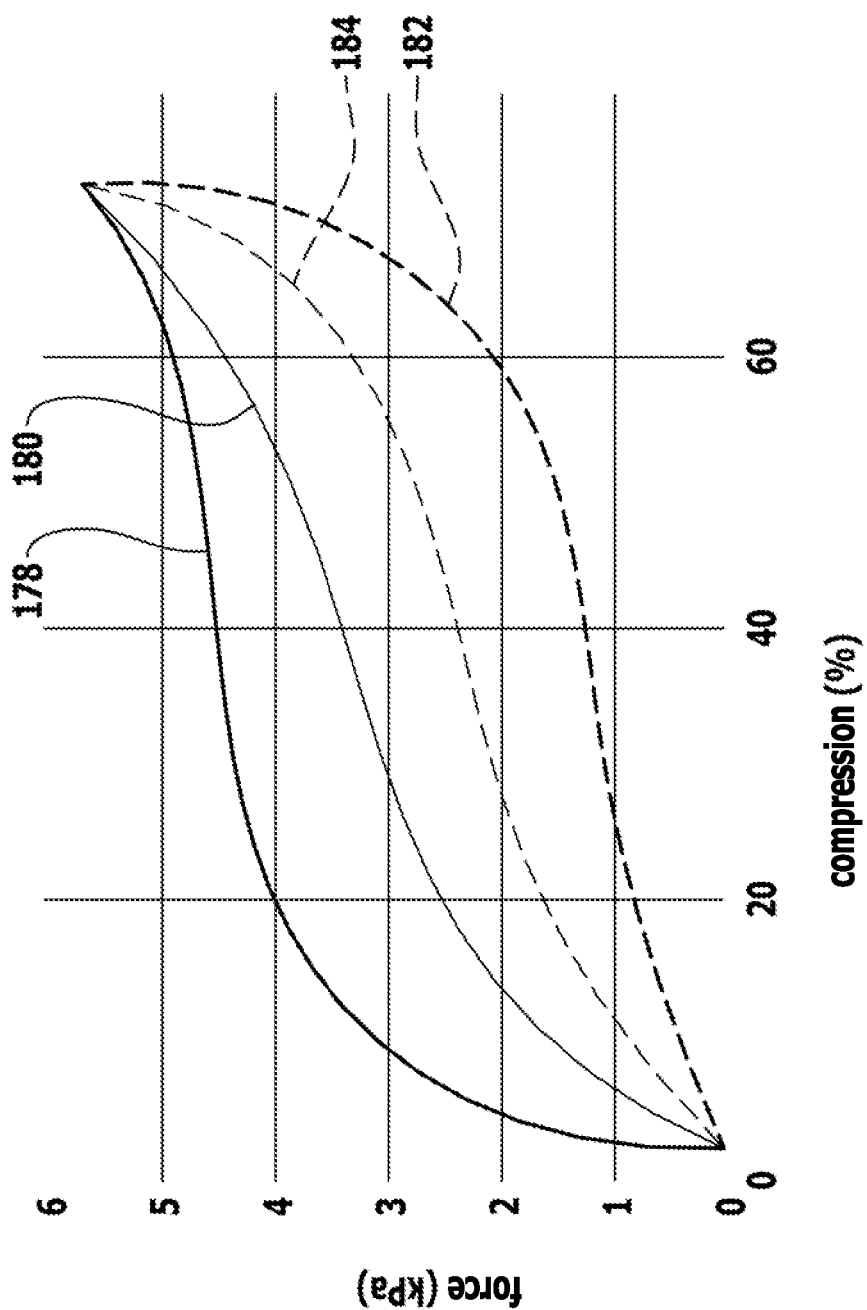
FIG. 7 shows a diagram to illustrate the properties of a viscoelastic material.

To clarify the mechanical properties of the viscoelastic material for use as material for the clip holder 100, the force is plotted against the compression of the material in the diagram shown in FIG. 7.

A standard foam material was used as comparative material for comparison of the properties.

As shown in FIG. 7, a load curve 178 of the viscoelastic material is located clearly above a load curve 180 of the standard foam material. This means that in comparison with compression of the standard foam material, a substantially higher force is required to compress the viscoelastic material.

The different return in shape to the original state is apparent from a relief curve 182 of the viscoelastic material, which is located clearly below a relief curve 184 of the standard foam material.

The large hysteresis of the load curve 178 and the relief curve 182 of the viscoelastic material occurring with the load and with the relief reflects the slow return to the original shape brought about by the at least one damping device 126.

Particularly easy removal of the clip 102 from the clip holder 100 is made possible by the at least one holding device 122 comprising at least one damping device 126, counteracting the at least one restoring device 128, to damp movement of the at least two holding surface areas 124 relative to each other from the deflected position in the direction back into the initial position.

The invention claimed is:

1. Medical or surgical clip holder, comprising:
    at least one medical or surgical clip, and
    at least one holding device for holding the at least one medical or surgical clip, said at least one holding device comprising:
        at least two holding surface areas movable relative to each other for holding the at least one clip with at least one of force locking and positive locking,
        at least one restoring device for moving the at least two holding surface areas relative to each other, such that, after deflection from an initial position, in which the at least two holding surface areas are in a predefined position relative to each other, into a deflected position, the at least one restoring device moves the at least two holding surface areas from the deflected position back to the initial position, and
        at least one damping device counteracting said at least one restoring device for damping a movement of the at least two holding surface areas relative to each other from the deflected position back to the initial position.

2. Clip holder in accordance with claim 1, further comprising a main body, wherein at least one of the at least two holding surface areas is configured so as to be movable relative to the main body.

3. Clip holder in accordance with claim 1, wherein the at least one holding device comprises a supporting surface for the at least one clip.

4. Clip holder in accordance with claim 3, wherein at least one of the at least two holding surface areas is configured so as to be movable in the direction of the supporting surface or so as to be movable away from the supporting surface.

5. Clip holder in accordance with claim 3, further comprising at least one supporting element, a surface of which forms at least part of the supporting surface for the at least one clip.

6. Clip holder in accordance with claim 1, wherein the at least two holding surface areas are arranged so as to face each other or so as to face away from each other.

7. Clip holder in accordance with claim 1, wherein the at least two holding surface areas are movable away from each other or towards each other out of the initial position.

8. Clip holder in accordance with claim 1, wherein the at least one holding device comprises at least one holding element, a surface of which forms at least part of at least one of the at least two holding surface areas.

9. Clip holder in accordance with claim 8, wherein the at least one holding element comprises a top layer, a surface of which forms at least part of at least one of the at least two holding surface areas.

10. Clip holder in accordance with claim 1, wherein the at least one restoring device and the at least one damping device are separate components of the at least one holding device or the at least one restoring device is formed in one piece with the at least one damping device.

11. Clip holder in accordance with claim 1, wherein the at least one restoring device and the at least one damping device are made of the same material.

12. Clip holder in accordance with claim 11, wherein the material of the at least one restoring device and of the at least one damping device is a viscoelastic material.

13. Clip holder in accordance with claim 12, wherein the viscoelastic material comprises at least one of a foamed material and a porous material.

14. Clip holder in accordance with claim 12, wherein the viscoelastic material is a material which returns substantially completely to an original state following deformation.

15. Clip holder in accordance with claim 12, wherein the viscoelastic material has a relaxation time of at least one of at least approximately 0.5 seconds and, at most, approximately 2 seconds, which elapses following deformation of the viscoelastic material up until at least partial restoration of an original state.

16. Clip holder in accordance with claim 12, wherein the at least one holding device comprises a viscoelastic material or is made of a viscoelastic material.

17. Clip holder in accordance with claim 1, wherein the at least one clip comprises two legs which include an original angle of less than 180° with each other.

18. Clip holder in accordance with claim 17, wherein the at least one clip comprises a restoring device for restoring the original angle included by the two legs following deformation of the at least one clip.

19. Clip holder in accordance with claim 18, wherein a relaxation time of the at least one clip, which elapses following deformation of the at least one clip up until at least partial restoration of the original angle included by the two legs, is less than a relaxation time of the at least one holding device, which elapses following deflection of the at least two holding surface areas relative to each other up until at least partial return to the initial position.

20. Clip holder in accordance with claim 1, wherein the clip holder comprises at least one coupling device for coupling the at least one clip to the at least one holding device.

21. Clip holder in accordance with claim 20, wherein the coupling device comprises at least two coupling elements which are adapted to be brought into engagement with each other in a storage position of the at least one holding device in which the at least one clip is held on the at least one holding device.

22. Use of a medical or surgical clip holder, comprising at least one holding device for holding at least one medical or surgical clip, said at least one holding device comprising:
    at least two holding surface areas movable relative to each other for holding the at least one clip with at least one of force locking and positive locking;
    at least one restoring device for moving the at least two holding surface areas relative to each other such that, after deflection from an initial position, in which the at least two holding surface areas are in a predefined position relative to each other, into a deflected position, the at least one restoring device moves the at least two holding surface areas from the deflected position back to the initial position; and at least one damping device counteracting said at least one restoring device for damping a movement of the at least two holding surface areas relative to each other from the deflected position back to the initial position for performing a method of removing a medical or surgical clip from a holding device of a medical or surgical clip holder for at least one medical or surgical clip, wherein the at least two holding surface areas of the holding device are deflected relative to each other to release a connection with the at least one of force locking and positive locking between the clip and the holding device, and wherein the clip is removed from the holding device before the at least two holding surface areas return to the initial position existing before deflection.

* * * * *